United States Patent [19]

Hazama et al.

[11] 4,403,096
[45] Sep. 6, 1983

[54] OPTICALLY ACTIVE IMIDAZOLIDIN-2-ONE DERIVATIVES

[75] Inventors: Motoo Hazama, Kyoto; Tadatoshi Aratani, Nishinomiya; Gohu Suzukamo, Ibaraki; Takeo Takahashi, Takarazuka, all of Japan

[73] Assignee: Sumitomo Chemical Company, Limited, Osaka, Japan

[21] Appl. No.: 278,350

[22] Filed: Jun. 29, 1981

[30] Foreign Application Priority Data

Jul. 10, 1980 [JP] Japan .................................. 55-95818

[51] Int. Cl.$^3$ .......................................... C07D 233/34
[52] U.S. Cl. ................................... 548/321; 548/303; 548/304
[58] Field of Search ........................................ 548/321

[56] References Cited

U.S. PATENT DOCUMENTS 3,700,659 10/1972 Gerecke et al. ................ 548/321 X
3,876,656  4/1975 Aoki et al. ...................... 548/321 X
4,014,895  3/1977 Aoki et al. ...................... 548/321 X

OTHER PUBLICATIONS

Ohrui, H., et al., *Tetrahedron Letters*, No. 32, pp. 2765–2766 (1975).
Confalone, P., et al., *Journal of the American Chemical Society*, vol. 97, pp. 5936–5938, (1975).
Morrison, J., et al., *Asymmetric Organic Reactions*, Prentice Hall, New York, 1970, pp. 419–424.
*Chemical Abstracts*, 83:28227s (1975) [Japan. Kokai 74,127,994, Aoki et al., 12/07/74].
March, J., *Advanced Organic Chemistry*, McGraw Hill, New York, 1968, pp. 336–337.

*Primary Examiner*—Richard A. Schwartz
*Attorney, Agent, or Firm*—Birch, Stewart, Kolasch & Birch

[57] ABSTRACT

A novel optically active cis-4,5-disubstituted imidazolidin-2-one derivative of the formula:

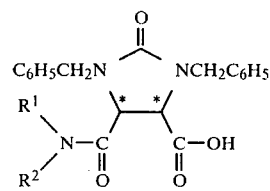

wherein $R^1$ is a $C_1$–$C_4$ alkyl group or benzyl and $R^2$ is a chiral aralkyl group optionally having at least one of $C_1$–$C_4$ alkyl, $C_1$–$C_4$ alkoxy and hydroxyl groups is produced asymmetrically by the reaction of 1,3-dibenzyl-cis-4,5-dicarboxy-imidazolidin-2-one or its anhydride with an optically active secondary amine of the formula:

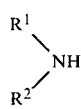

wherein $R^1$ and $R^2$ are each as defined above and is transformed into the lactone of 1,3-dibenzyl-cis-4-carboxy-5-hydroxymethyl-imidazolidin-2-one, which is a key intermediate in the synthesis of d-biotin.

7 Claims, No Drawings

OPTICALLY ACTIVE IMIDAZOLIDIN-2-ONE DERIVATIVES

The present invention relates to novel optically active imidazolidin-2-one derivatives and their production.

More particularly, it relates to optically active cis-4,5-disubstituted imidazolidin-2-one derivatives of the formula:

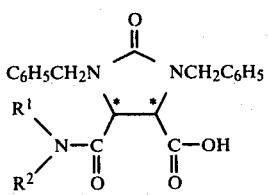

wherein $R^1$ is a $C_1$–$C_4$ alkyl group or benzyl and $R^2$ is a chiral aralkyl group optionally having at least one of $C_1$–$C_4$ alkyl, $C_1$–$C_4$ alkoxy and hydroxyl groups, and their production.

The said optically active imidazolidin-2-one derivatives (I) are novel and useful as intermediates in the synthesis of d-biotin and trimethaphan camphorsulfonate.

d-Biotin is known as Vitamin H and is widely used as a medicine and also as a feed additive. The bistin molecule has three asymmetric carbon atoms, and there can be eight stereoisomers including optical isomers. Among them, however, only d-biotin, whose structure is shown below, is biologically active, and otheer isomers are almost inactive.

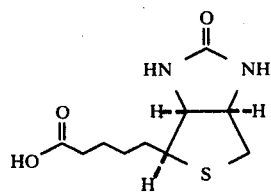

For stereo-specific synthesis of optically active biotin, various methods are known. For instance, a method using D-mannose (Tetrahedron Letters, page 2765 (1975)) or L-cysteine as the starting material (J.Am.-Chem.Soc., 97, 5936 (1975)) has been reported. In this method, optically active starting materials are converted into optically active biotin in a stereo-specific manner. This process is advantageous in not including any resolution step but is difficult to apply on an industrial scale in requiring many reaction sequences and affording optically active biotin only in poor yields.

There is another method using an optically active lactone of the following formula (II) as an intermediate.

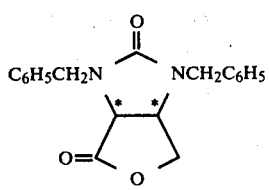

In this method, an optically active intermediate is employed at a relatively early stage in the total synthesis of biotin and unnecessary antipodes are not produced at a later stage.

For the production of the optically active lactone (II), many methods are available, among which the following two are typical. The first method is disclosed in Japanese Patent Publication (examined) No. 32551/1974, U.S. Pat. No. 3,700,659, etc., in which the dicarboxylic acid anhydride (III) having a cis configuration is reacted with optically active cholesterol or cyclohexanol and the resultant diastereomeric half ester (IV) is resolved with the aid of triethylamine or l-ephedrine, respectively, to give the half ester (IV) in an optically pure form. Reduction of the resolved half ester (IV), followed by lactonization gives the optically pure lactone (II). The above chemical conversion is represented by the following equation:

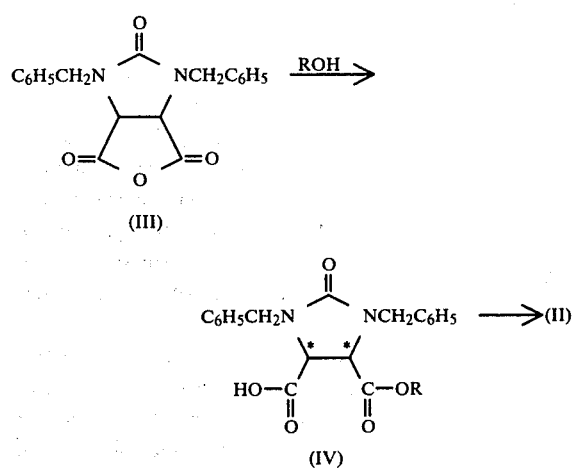

wherein R is cholesteryl or cyclohexyl. However, this method is disadvantageous in requiring a resolution step which is complex and inefficient. Although the unnecessary diastereomer of the half ester (IV) is hydrolyzed and dehydrated to give back the anhydride (III) for repeated use, the amount of the desired diastereomer never exceeds that of the unnecessary diastereomer separated.

The second method is disclosed in Japanese Patent Publication (unexamined) Nos. 20196/1974, 117,467/1974 and 127,994/1974, U.S. Pat. Nos. 3,876,656 and 4,014,895. etc., in which the dicarboxylic acid (V) having a cis configuration is reacted with an optically active primary amine ($R'$-$NH_2$), and the resulting imide (VI) is reduced with a metal hydride to give an amide-alcohol (VII). Hydrolysis of the amide-alcohol (VII), followed by lactonization gives the optically active lactone (II). The above chemical conversion is represented by the following equation:

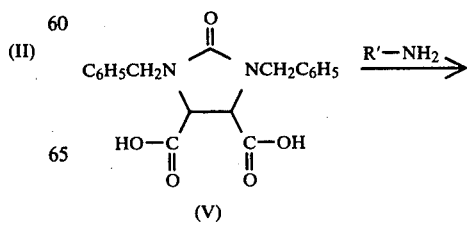

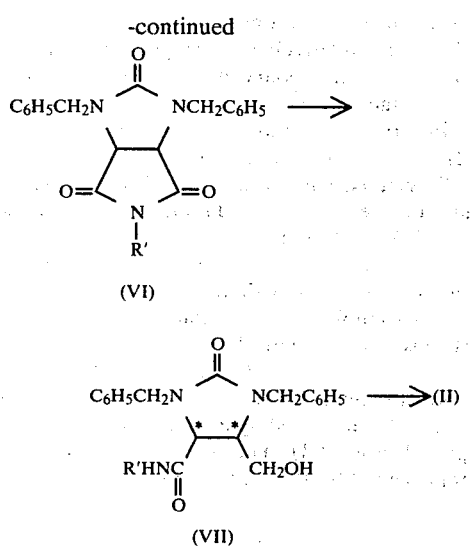

(VI)

(VII)

In this method, the attack of a metal hydride on the two carbonyl groups of the imide molecule (VI) is influenced by the chiral moiety R′, and one of the diastereomers of the amide-alcohol (VII) is produced much more than the other diastereomer. Thus, asymmetric induction is achieved in the above process. By the suitable choice of the optically active primary amine (R′—NH$_2$), a maximum optical yield of 75 to 80% has been obtained.

As a result of the extensive study on the asymmetric synthesis of the optically active lactone (II), we have accomplished the following invention. The reaction of the dicarboxylic acid (V) or the anhydride (III) with an optically active secondary amine of the formula:

$$\begin{array}{c} R^1 \\ \phantom{R^1}\diagdown \\ \phantom{RR}NH \\ \phantom{R^1}\diagup \\ R^2 \end{array} \quad (VIII)$$

wherein $R^1$ and $R^2$ are each as defined above proceeds asymmetrically to give the optically active imidazolidin-2-one derivative (I) (hereinafter referred to as "amide-carboxylic acid (I)") in a high optical yield. It has also been found that the optically active amide-carboxylic acid (I) can be converted into the optically active lactone (II) in an excellent yield.

The optically active amide-carboxylic acid (I) obtained in the above reaction contains one of the diastereomers (Ia) in a much larger or smaller amount than the other diastereomer (Ib).

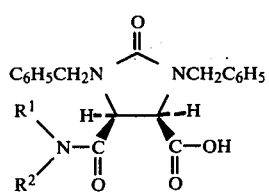

(Ia)

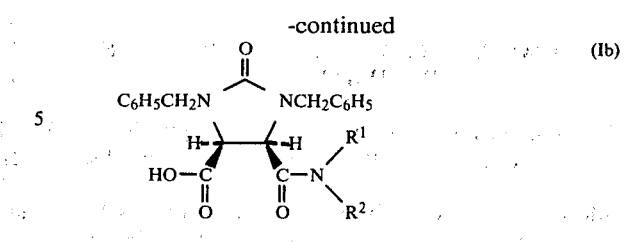

(Ib)

The optical yield (Y) in percent is represented by the following equation:

$$Y = [Y(Ia) - Y(Ib)] / [Y(Ia) + Y(Ib)] \times 100$$

wherein Y(Ia) and Y(Ib) represent the yields of the diastereomer (Ia) and the diastereomer (Ib), respectively.

This type of asymmetric reaction belongs to asymmetric synthesis starting from a meso compound differentiating the enantio-field (Y. Izumi and A. Tai: "Stereo-differentiating Reactions", Academic Press, New York, 1977), and a high optical yield as much as 90% has not been reported. The high optical yield achieved reminds us of a complete selectivity found in the biological systems involving microorganisms or enzymes (J. B. Jones et al.: "Techniques of Chemistry", published by John Wiley & Sons, Vol. 10, 1976, pages 107–401).

For transformation of the optically active amide-carboxylic acid (I) to the optically active lactone (II), various procedures are possible. In a typical procedure, the optically active amide-carboxylic acid (I) is esterified to give the amide-carboxylic ester (IX), which is reduced with a metal hydride such as sodium borohydride to an amide-alcohol (X). Acidic hydrolysis of the amide-alcohol (X), followed by lactonization gives the optically active lactone (II). These chemical conversions are shown by the following equation:

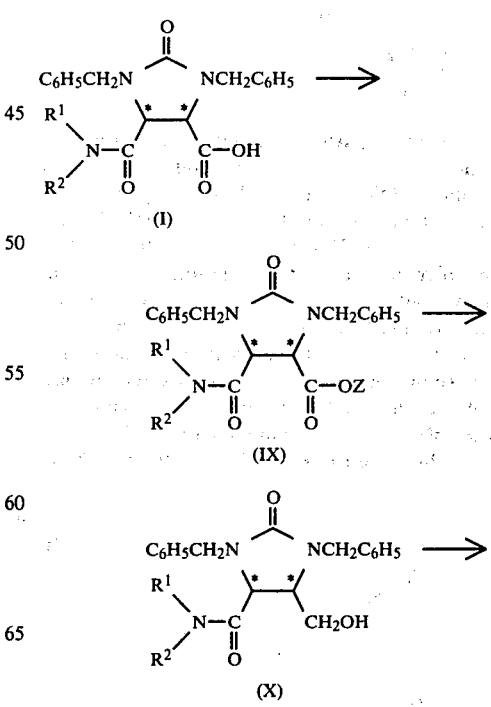

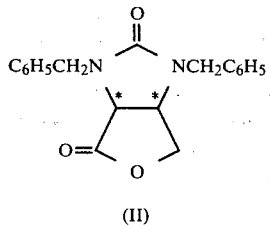

(II)

wherein Z is a lower alkyl group and $R^1$ and $R^2$ are each as defined above.

In the above chemical conversions, the racemization at the asymmetric carbon atoms is impossible, and all the transformations are carried out to completion so that the proportion of (Ia)/(Ib) in the amide-carboxylic acid (I) is expected to be equal to that of the enantiomers of the lactone (II). Thus, the optical yield of the amide-carboxylic acid (I) is considered to be equal to the optical purity of the lactone (II).

The optically active secondary amine (VIII) used for the production of the amide-carboxylic acid (I) is recovered on acidic hydrolysis of the amide-alcohol (X) without racemization and can be used again.

In order to raise the optical purity of the lactone (II), the diastereomeric amide-carboxylic acid (I), its salt or amide-ester (IX) can be purified by an appropriate operation such as column chromatography on a suitable adsorbent or recrystallization from a proper solvent. The unnecessary diastereomer separated can be readily hydrolyzed to recover the dicarboxylic acid (V) and the optically active secondary amine.

The recovered dicarboxylic acid (V) may be used again as the starting material as itself or the corresponding dicarboxylic anhydride (III). Also, the optically active secondary amine (VIII) may be recycled by itself. Therefore, the entire amount of the starting material, (III) or (V), can be ultimately converted into the desired diastereomer of the optically active amide-carboxylic acid (I) or its ester (IX).

The dicarboxylic acid (V) and the dicarboxylic anhydride (III) are known compounds as are disclosed in U.S. Pat. No. 2,489,232.

With respect to the optically active secondary amine (VII), $R^1$ is a $C_1$-$C_4$ alkyl group (e.g. methyl, ethyl, n-propyl, isopropyl, n-butyl, isobutyl) or a benzyl group. The substituent $R^1$ can be introduced into the optically active primary amine of the formula: $R^2$—$NH_2$ by alkylation or benzylation.

$R^2$ is a chiral aralkyl group optionally having at least one of $C_1$-$C_4$ alkyl (e.g. methyl, ethyl, n-propyl, isopropyl, n-butyl, isobutyl), $C_1$-$C_4$ alkoxy (e.g. methoxy, ethoxy, propoxy, isopropoxy, butoxy) and hydroxyl groups. The aryl moiety in the aralkyl group may be phenyl, naphthyl, etc., and the alkyl moiety may be lower alkyl such as methyl, ethyl, n-propyl, isopropyl, n-butyl, isobutyl, etc. Specific examples of the said aralkyl group are 1-phenylethyl, 1-(α-naphthyl)ethyl, 1-phenyl-2-(p-tolyl)ethyl, etc.

As $R^2$, the aralkyl group representable by the following formula is particularly preferred:

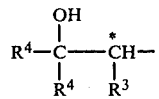

wherein the carbon atom accompanied with an asterisk (*) is an asymmetric carbon atom, and $R^3$ is $C_1$-$C_4$ alkyl (e.g. methyl, ethyl, n-propyl, isopropyl, n-butyl, isobutyl, t-butyl), phenyl or benzyl and $R^4$ is benzyl or phenyl optionally bearing at least one of $C_1$-$C_4$ alkyl (e.g. methyl, ethyl, n-propyl, isopropyl, n-butyl, isobutyl, t-butyl) and $C_1$-$C_4$ alkoxy (e.g. methoxy, ethoxy, n-propoxy, isopropoxy, n-butoxy, isobutoxy). Thus, specific examples of the substituent $R^4$ are benzyl, phenyl, 2-methoxyphenyl, 2-isopropoxyphenyl, 2-isopropoxy-5-methylphenyl, etc.

Accordingly, specific examples of the optically active secondary amine (VIII) include the following:

N-Methyl-1-phenylethylamine;
N-Benzyl-1-phenylethylamine;
N-Methyl-1-(α-naphthyl)ethylamine;
N-Benzyl-1-(α-naphthyl)ethylamine;
N-Methyl-1-phenyl-2-(p-tolyl)ethylamine;
N-Benzyl-1-phenyl-2-(p-tolyl)ethylamine;
N-Methyl-2-amino-1,1-diphenyl-1-propanol;
N-Ethyl-2-amino-1,1-diphenyl-1-propanol;
N-Benzyl-2-amino-1,1-diphenyl-1-propanol;
N-Methyl-2-amino-1,1-dibenzyl-1-propanol;
N-Methyl-2-amino-1,1-diphenyl-4-methyl-1-pentanol;
N-Methyl-2-amino-1,1-dibenzyl-4-methyl-1-pentanol;
N-Methyl-2-amino-1,1,2-triphenylethanol;
N-Methyl-2-amino-1,1-di(2-isopropoxyphenyl)-3-phenyl-1-propanol;
N-Methyl-2-amino-1,1-di(2-methoxyphenyl)-1-propanol;
N-Methyl-2-amino-1,1-di(2-isopropoxy-5-methylphenyl)-3-phenyl-1-propanol;
N-Methyl-2-amino-1,1,3-triphenyl-1-propanol; etc.

The chiral amine (VIII) having either (R)- or (S)-configuration can be employed.

The reaction of the dicarboxylic acid (V) or the anhydride (III) with the optically active secondary amine (VIII) is usually carried out in a solvent inert to the said starting materials under the reaction conditions. Examples of such a solvent include aromatic hydrocarbons (e.g. benzene, toluene, xylene), ethers (e.g. diethyl ether, tetrahydrofuran, dioxane, 1,2-dimethoxyethane, diethyleneglycol dimethyl ether), etc. The addition of a basic substance such as a tertiary amine (e.g. triethylamine, tributylamine) as well as pyridine to the reaction system is usually preferred.

Strict limitation is not present on the reaction temperature. When the dicarboxylic anhydride (III) is used as the starting material, the reaction is usually effected at a temperature ranging from −20° C. to the boiling point of the solvent, preferably at −20°~40° C. When the dicarboxylic acid (V) is employed as the starting material, it is advantageous to carry out the reaction under continuous removal of water by azeotropic distillation. Alternatively, a dehydrating agent such as molecular sieve or dicyclohexylcarbodiimide may be employed.

The reaction time is influenced by the starting material, the solvent, the reaction temperature, etc. When the reaction is carried out using the dicarboxylic acid (V) at the boiling temperature of the solvent, it will usually take 1 to 20 hours. When the reaction is effected using the anhydride (III) at about 25° C., it ordinarily takes 10 to 48 hours.

The molar ratio of the dicarboxylic acid (V) or the dicarboxylic anhydride (III) to the optically active secondary amine (VIII) is preferred to be nearly 1.0, particularly between 0.8 and 1.2.

Separation and purification of the reaction product from the reaction mixture may be accomplished by per se conventional procedures such as distillation of the solvent, extraction with a proper solvent, washing, chromatography, etc. The progress of the reaction may be traced by the use of a thin layer chromatography or a high pressure liquid chromatography. The yield is almost quantitative.

Specific examples of the optically active amide-carboxylic acid (I) as prepared by the above method are as follows:

1,3-Dibenzyl-cis-4-carboxy-5-[N-methyl-N-(1-phenylethyl)carbamoyl]imidazolidin-2-one;
1,3-Dibenzyl-cis-4-carboxy-5-[N-benzyl-N-(1-phenylethyl)carbamoyl]imidazolidin-2-one;
1,3-Dibenzyl-cis-4-carboxy-5-[N-methyl-N-{1-(α-naphthyl)ethyl}carbamoyl]imidazolidin-2-one;
1,3-Dibenzyl-cis-4-carboxy-5-[N-benzyl-N-{1-(α-naphthyl)ethyl}carbamoyl]imidazolidin-2-one;
1,3-Dibenzyl-cis-4-carboxy-5-[N-methyl-N-{1-phenyl-2-(p-tolyl)ethyl}carbamoyl]imidazolidin-2-one;
1,3-Dibenzyl-cis-4-carboxy-5-[N-benzyl-N-{1-phenyl-2-(p-tolyl)ethyl}carbamoyl]imidazolidin-2-one;
1,3-Dibenzyl-cis-4-carboxy-5-[N-methyl-N-(1-methyl-2,2-diphenyl-2-hydroxyethyl)carbamoyl]imidazolidin-2-one;
1,3-Dibenzyl-cis-4-carboxy-5-[N-ethyl-N-(1-methyl-2,2-diphenyl-2-hydroxyethyl)carbamoyl]imidazolidin-2-one;
1,3-Dibenzyl-cis-4-carboxy-5-[N-benzyl-N-(1-methyl-2,2-diphenyl-2-hydroxyethyl)carbamoyl]imidazolidin-2-one;
1,3-Dibenzyl-cis-4-carboxy-5-[N-methyl-N-(1-methyl-2,2-dibenzyl-2-hydroxyethyl)carbamoyl]imidazolidin-2-one;
1,3-Dibenzyl-cis-4-carboxy-5-[N-methyl-N-(1-isobutyl-2,2-diphenyl-2-hydroxyethyl)carbamoyl]imidazolidin-2-one;
1,3-Dibenzyl-cis-4-carboxy-5-[N-methyl-N-(1-isobutyl-2,2-dibenzyl-2-hydroxyethyl)carbamoyl]imidazolidin-2-one;
1,3-Dibenzyl-cis-4-carboxy-5-[N-methyl-N-(1,2,2-triphenyl-2-hydroxyethyl)carbamoyl]imidazolidin-2-one;
1,3-Dibenzyl-cis-4-carboxy-5-[N-methyl-N-{1-benzyl-2,2-di(2-isopropoxyphenyl)-2-hydroxyethyl}carbamoyl]imidazolidin-2-one;
1,3-Dibenzyl-cis-4-carboxy-5-[N-methyl-N-{1-methyl-2,2-di(2-methoxyphenyl)-2-hydroxyethyl}carbamoyl]imidazolidin-2-one;
1,3-Dibenzyl-cis-4-carboxy-5-[N-methyl-N-{1-benzyl-2,2-di(2-isopropoxy-5-methylphenyl)-2-hydroxyethyl}carbamoyl]imidazolidin-2-one;
1,3-Dibenzyl-cis-4-carboxy-5-[N-methyl-N-(1-benzyl-2,2-diphenyl-2-hydroxyethyl)carbamoyl]imidazolidin-2-one; etc.

The present invention will be illustrated more in detail by the following Examples and Reference Examples.

EXAMPLE 1

A solution of (S)-N-methyl-1-phenylethylamine (1.35 g; 10 mmol) and triethylamine (1.01 g; 10 mmol) in tetrahydrofuran (10 ml) was added dropwise to a suspension of the anhydride (III) (3.36 g; 10 mmol) in tetrahydrofuran (30 ml) at 25° C. with stirring in 30 minutes to give a homogeneous solution. After stirring at 25° C. for 48 hours, the solvent was distilled in vacuo. The residue was dissolved in chloroform (30 ml), washed with N-hydrochloric acid (30 ml) and a saturated solution of sodium chloride, dried over anhydrous sodium sulfate and concentrated to give 1,3-dibenzyl-cis-4-carboxy-5-[N-methyl-N-(S)-(1-phenylethyl)carbamoyl]imidazolidin-2-one (4.48 g). Yield, 95.1%.

IR: $\nu_{CO}$ 1740, 1710, 1660, 1640 cm$^{-1}$. M.P., 74.8° C. $[\alpha]_D$ −26.2° (C=1, CHCl$_3$).

EXAMPLE 2

A mixture of (R)-N-methyl-1-phenylethylamine (1.35 g; 10 mmol) and the dicarboxylic acid (V) (3.54 g; 10 mmol) in xylene (50 ml) was heated under reflux for 4 hours with azeotropic removal of water. Evaporation of the solvent gave 1,3-dibenzyl-cis-4-carboxy-5-[N-methyl-N-(R)-(1-phenylethyl)carbamoyl]imidazolidin-2-one (4.66 g). Yield, 99.0%. M.P., 73.5° C. $[\alpha]_D$ +29.0° (C=1, CHCl$_3$).

REFERENCE EXAMPLE 1

1,3-Dibenzyl-cis-4-carboxy-5-[N-methyl-N-(S)-(1-phenylethyl)carbamoyl]imidazolidin-2-one (4.48 g, Example 1) was dissolved in methanol (50 ml) containing hydrogen chloride (20% by weight) and left at 25° C. for 24 hours. Distilling of the solvent gave 1,3-dibenzyl-cis-4-methoxycarbonyl-5-[N-methyl-N-(S)-(1-phenylethyl)carbamoyl]imidazolidin-2-one (4.52 g). Yield, 98.0%. M.P., 113.8° C. $[\alpha]_D$ −21.3° (C=1, CHCl$_3$). IR: $\nu_{CO}$ 1760, 1720, 1700, 1640 cm$^{-1}$.

REFERENCE EXAMPLE 2

1,3-Dibenzyl-cis-4-carboxy-5-[N-methyl-N-(S)-(1-phenylethyl)carbamoyl]imidazolidin-2-one (4.48 g, Example 1) was dissolved in tetrahydrofuran (50 ml), and a solution of diazomethane (0.42 g) in ethyl ether (50 ml) was added dropwise thereto. By distilling off the solvent, there was obtained 1,3-dibenzyl-cis-4-methoxycarbonyl-5-[N-methyl-N-(S)-(1-phenylethyl)carbamoyl]imidazolidin-2-one (4.52 g). Yield, 98.0%.

REFERENCE EXAMPLE 3

1,3-Dibenzyl-cis-4-methoxycarbonyl-5-[N-methyl-N-(S)-(1-phenylethyl)carbamoyl]imidazolidin-2-one (4.52 g, Reference Example 2) was dissolved in tetrahydrofuran (40 ml), a solution of sodium borohydride (1.14 g) in water (10 ml) was added thereto, and the mixture was stirred at room temperature for 48 hours. To the reaction mixture, N hydrochloric acid (30 ml) was added, and the solvent was distilled off. The residue was extracted with chloroform, washed with N hydrochloric acid and a saturated solution of sodium chloride, dried over anhydrous sodium sulfate and concentrated to give 1,3-dibenzyl-cis-4-hydroxymethyl-5-N-methyl-N-(S)-(1-phenylethyl)carbamoyl]imidazolidin-2-one (3.83 g). Yield, 90.5%. $[\alpha]_D$ −44.6° (C=0.8, CHCl$_3$). IR: $\nu_{OH}$ 3400 cm$^{-1}$; $\nu_{CO}$ 1700, 1600, 1550 cm$^{-1}$.

REFERENCE EXAMPLE 4

A mixture of 1,3-dibenzyl-cis-4-hydroxymethyl-5-[N-methyl-N-(S)-(1-phenylethyl)carbamoyl]imidazolidin-2-one (3.83 g), dioxane (40 ml) and 20% sulfuric acid (30 ml) was refluxed for 5 hours. After distilling off the solvent, the residue was extracted with chloroform (30 ml). The chloroform extract was washed with N hydrochloric acid (30 ml×2) and then with a saturated solution of sodium chloride, dried over anhydrous sodium sulfate and concentrated. The residue was subjected to column chromatography on silica gel, and elution with toluene-ether (10:1) gave the lactone (II) (2.41 g). Yield, 75.0% (based on the anhydride (III)). M.P., 107.6° C. $[\alpha]_D$ −16.8° (C=1, CHCl$_3$). The optical purity of the lactone (II) was calculated to be 27.0% (based on $[\alpha]_D$ −62.3° for the optically pure sample).

REFERENCE EXAMPLE 5

The aqueous solution containing 20% sulfuric acid and N hydrochloric acid in Reference Example 4 was made alkanine (pH 12) with a 10% aqueous solution of sodium hydroxide. The separated oil was extracted with ethyl ether, washed with water, dried over anhydrous sodium sulfate and concentrated to give (S)-N-methyl-1-phenylethylamine (1.00 g). Recovery, 90%. $[\alpha]_D$ −63.0° (C=2.7, ethanol).

REFERENCE EXAMPLE 6

1,3-Dibenzyl-cis-4-carboxy-5-[N-methyl-N-(R)-(1-phenylethyl)carbamoyl]imidazolidin-2-one (4.66 g) obtained in Example 2 was subjected to esterification, hydrolysis and lactonization, respectively, as in Reference Examples 1, 3 and 4 to give the lactone (II) (2.25 g). Yield, 70.0% (based on the dicarboxylic acid (V)). M.P. 106.9° C. $[\alpha]_D$ +13.4° (C=1, CHCl$_3$). Optical purity, 21.5%.

EXAMPLE 3

1,3-Dibenzyl-cis-4-carboxy-5-[N-methyl-N-(S)-(1-phenylethyl)carbamoyl]imidazolidin-2-one (2.2 g) obtained in Example 1 was recrystallized from a mixture of chloroform (10 ml), ethyl acetate (30 ml) and n-hexane (60 ml) to give a purified product (0.96 g). Yield of recrystallization, 43.6%. M.P., 189.8° C. $[\alpha]_D$ −7.9° (C=1, CHCl$_3$).

REFERENCE EXAMPLE 7

1,3-Dibenzyl-cis-4-carboxy-5-[N-methyl-N-(S)-(1-phenylethyl)carbamoyl]imidazolidin-2-one (0.96 g) obtained in Example 3 was converted into the lactone (II) (0.53 g) as in Reference Examples 2, 3 and 4. Yield, 35.2% (based on the anhydride (III)). M.P., 113.2° C. $[\alpha]_D$ −54.8° (C=1, CHCl$_3$). Optical purity, 88.0%.

REFERENCE EXAMPLE 8

1,3-Dibenzyl-cis-4-methoxycarbonyl-5-[N-methyl-N-(S)-(1-phenylethyl)carbamoyl]imidazolidin-2-one (4.0 g, Reference Example 1) was recrystallized from a mixture of chloroform (10 ml) and n-hexane (40 ml) to give a purified product (1.85 g). Yield of recrystallization, 46.3%. M.P., 142.4° C. $[\alpha]_D$ −2.6° (C=1, CHCl$_3$).

REFERENCE EXAMPLE 9

1,3-Dibenzyl-4-methoxycarbonyl-5-[N-methyl-N-(S)-(1-phenylethyl)carbamoyl]imidazolidin-2-one (1.85 g) obtained in Reference Example 8 was converted into the lactone (II) (0.98 g) as in Reference Examples 3 and 4. Yield, 34.4% (based on the anhydride (III)). M.P., 117.4° C. $[\alpha]_D$ −59.1° (C=1, CHCl$_3$). Optical purity, 94.9%.

EXAMPLES 4 TO 16

In the same manner as in Example 1, the anhydride (III) was reacted with an optically active secondary amine (VIII) to give the compound (I). The results are shown in Table 1.

REFERENCE EXAMPLES 10 TO 22

The compounds (I) obtained in Examples 4 to 16 were converted into the lactone (II) by a series of the treatments as in Reference Examples 2, 3 and 4. The results are shown in Table 1.

TABLE 1

| Example | Optically active secondary amine | Compound (I) | Properties of Compound (I) Yield (%) | M.P. (°C.) | $[\alpha]_D$ (°) | Reference Example | Lactone (II) Yield (%)* | M.P. (°C.) | $[\alpha]_D$ (°) | Optical purity (%) |
|---|---|---|---|---|---|---|---|---|---|---|
| 4 | (S)-N-Benzyl-1-phenylethylamine | 1,3-Dibenzyl-cis-4-carboxy-5-[N-benzyl-N-(S)-(1-phenylethyl)-carbamoyl]imidazolidin-2-one | 94.3 | 81.7 | −42.3 | 10 | 39.8 | 106.5 | +28.0 | 44.9 |
| 5 | (S)-N-Methyl-1-(α-naphthyl)-ethylamine | 1,3-Dibenzyl-cis-4-carboxy-5-[N-methyl-N-(S)-{1-(α-naphthyl)-ethyl}carbamoyl]imidazolidin-2-one | 99.0 | 169.2 | −10.3 | 11 | 60.8 | 107.0 | −23.2 | 37.2 |
| 6 | (S)-N-Benzyl-1-(α-naphthyl)-ethylamine | 1,3-Dibenzyl-cis-4-carboxy-5-[N-benzyl-N-(S)-{1-(α-naphthyl)-ethyl}carbamoyl]imidazolidin-2-one | 100.0 | 77.5 | +32.3 | 12 | 21.5 | 106.5 | +20.8 | 33.3 |
| 7 | (S)-N-Methyl-1-phenyl-2-(p-tolyl)ethylamine | 1,3-Dibenzyl-cis-4-carboxy-5-[N-methyl-N-(S)-{1-phenyl-2-(p-tolyl)ethyl}carbamoyl]-imidazolidin-2-one | 88.4 | 83.5 | −47.4 | 13 | 64.6 | 107.1 | −18.9 | 30.3 |
| 8 | (S)-N-Benzyl-1-phenyl-2-(p-tolyl)ethylamine | 1,3-Dibenzyl-cis-carboxy-5-[N-benzyl-N-(S)-{1-phenyl-2-(p-tolyl)ethyl}carbamoyl]-imidazolidin-2-one | 99.5 | Oily product | +11.3 | 14 | 33.2 | 107.4 | +11.0 | 17.7 |
| 9 | (S)-N-Methyl-2-amino-1,1-diphenyl-1-propanol | 1,3-Dibenzyl-cis-4-carboxy-5-[N-methyl-N-(S)-(1-methyl-2,2-diphenyl-2-hydroxy-ethyl)carbamoyl]imidazolidin-2-one | 91.9 | 117.9 | −1.4 | 15 | 73.4 | 117.4 | −55.8 | 89.6 |

TABLE 1-continued

| Example | Optically active secondary amine | Compound (I) | Properties of Compound (I) | | | Reference Example | Lactone (II) | | | Optical purity (%) |
|---|---|---|---|---|---|---|---|---|---|---|
| | | | Yield (%) | M.P. (°C.) | $[\alpha]_D$ (°) | | Yield (%)* | M.P. (°C.) | $[\alpha]_D$ (°) | |
| 10 | (S)-N—Benzyl-2-amino-1,1-diphenyl-1-propanol | 1,3-Dibenzyl-cis-4-carboxy-5-[N—benzyl-N—(S)-(1-methyl-2,2-diphenyl-2-hydroxyethyl)carbamoyl]imidazolidin-2-one | 99.2 | 86.2 | +11.4 | 16 | 36.1 | 113.2 | −50.0 | 80.3 |
| 11 | (S)-N—Ethyl-2-amino-1,1-diphenyl-1-propanol | 1,3-Dibenzyl-cis-4-carboxy-5-[N—ethyl-N—(S)-(1-methyl-2,2-diphenyl-2-hydroxyethyl)carbamoyl]imidazolidin-2-one | 93.4 | 80.1 | +32.6 | 17 | 23.7 | 108.2 | −36.6 | 58.8 |
| 12 | (S)-N—Methyl-2-amino-1,1-dibenzyl-1-propanol | 1,3-Dibenzyl-cis-4-carboxy-5-[N—methyl-N—(S)-(1-methyl-2,2-dibenzyl-2-hydroxyethyl)carbamoyl]imidazolidin-2-one | 92.1 | 83.3 | +20.7 | 18 | 47.5 | 106.5 | −21.5 | 34.4 |
| 13 | (S)-N—Methyl-2-amino-1,1-diphenyl-4-methyl-1-pentanol | 1,3-Dibenzyl-cis-4-carboxy-5-[N—methyl-N—(S)-(1-isobutyl-2,2-diphenyl-2-hydroxyethyl)carbamoyl]imidazolidin-2-one | 100.1 | 102.9 | −4.3 | 19 | 67.8 | 105.4 | −26.4 | 42.2 |
| 14 | (S)-N—Methyl-2-amino-1,1-dibenzyl-4-methyl-1-pentanol | 1,3-Dibenzyl-cis-4-carboxy-5-[N—methyl-N—(S)-(1-isobutyl-2,2-dibenzyl-2-hydroxyethyl)carbamoyl]imidazolidin-2-one | 100 | 105.2 | +28.8 | 20 | 38.5 | 114.5 | −43.8 | 70.3 |
| 15 | (R)-N—Methyl-2-amino-1,1,2-triphenylethanol | 1,3-Dibenzyl-cis-4-carboxy-5-[N—methyl-N—(R)-(1,2,2-triphenyl-2-hydroxyethyl)carbamoyl]imidazolidin-2-one | 68.9 | 132.1 | +39.5 | 21 | 22.4 | 107.5 | +30.5 | 48.9 |
| 16 | (R)-N—Methyl-2-amino-1,1,3-triphenyl-1-propanol | 1,3-Dibenzyl-cis-4-carboxy-5-[N—methyl-N—(R)-(1-benzyl-2,2-diphenyl-2-hydroxyethyl)carbamoyl]imidazolidin-2-one | 102.9 | 83.4 | +27.8 | 22 | 30.7 | | +35.8 | 57.4 |
| 17 | (S)-N—Methyl-2-amino-1,1-di(2-methoxyphenyl)-1-propanol | 1,3-Dibenzyl-cis-4-carboxy-5-[N—methyl-N—(S)-{1-methyl-2,2-di(2-methoxyphenyl)-2-hydroxyethyl}carbamoyl]imidazolidin-2-one | 94.4 | 83.2 | −33.6 | 23 | 36.3 | 112.9 | −47.0 | 75.4 |
| 18 | (R)-N—Methyl-2-amino-1,1-di(2-isopropoxyphenyl)-3-phenyl-1-propanol | 1,3-Dibenzyl-cis-4-carboxy-5-[N—methyl-N—(R)-{1-methyl-2,2-di(2-isopropoxyphenyl)-2-hydroxyethyl}carbamoyl]imidazolidin-2-one | 91.5 | 78.6 | +36.9 | 24 | 40.5 | 112.5 | +45.7 | 73.3 |
| 19 | (R)-N—Methyl-2-amino-1,1-di(2-isopropoxy-5-methylphenyl)-3-phenyl-1-propanol | 1,3-Dibenzyl-cis-4-carboxy-5-[N—methyl-N—(R)-{1-methyl-2,2-di(2-isopropoxy-5-methylphenyl)-2-hydroxyethyl}carbamoyl]imidazolidin-2-one | 88.8 | 74.5 | +41.5 | 25 | 12.9 | 107.5 | +23.2 | 37.3 |

EXAMPLE 20

1,3-Dibenzyl-cis-4-carboxy-5-[N-methyl-N-(S)-{(1-methyl-2,2-diphenyl-2-hydroxy)ethyl}carbamoyl-]imidazolidin-2-one (5.77 g; 10 mmol) obtained in Example 9 and triethylamine (1.01 g; 10 mmol) were dissolved in hot isopropanol (30 ml), n-hexane (75 ml) was added thereto, and the resultant mixture was allowed to stand overnight at 0° C. The crystalline precipitates were collected by filtration and dried to give the triethylamine salt of the amide-carboxylic acid (I) (4.41 g). Yield, 65%. M.P., 177.4° C. $[\alpha]_D$ −46.1° (C=1.08, CHCl₃).

The said triethylamine salt (3.0 g) was mixed with N hydrochloric acid (20 ml), and the mixture was extracted with ethyl acetate and evaporated to give 1,3-dibenzyl-cis-4-carboxy-5-[N-methyl-N-(S)-{(1-methyl-2,2-diphenyl-2-hydroxy)ethyl}carbamoyl-]imidazolidin-2-one (2.46 g). Yield, 96.5%. M.P., 115.5° C. $[\alpha]_D$ +1.6° (C=1.15, CHCl₃).

REFERENCE EXAMPLE 26

1,3-Dibenzyl-cis-4-carboxy-5-[N-methyl-N-(S)-{(1-methyl-2,2-diphenyl-2-hydroxy)ethyl}carbamoyl]imidazolidin-2-one (2.00 g, Example 20) was converted into the lactone (II) (0.81 g) as in Reference Examples 2, 3 and 4. Yield, 72.8%. M.P., 121.2° C. $[\alpha]_D$ −62.7°. Optical purity, 100%.

What is claimed is:

1. An optically active cis-4,5-disubstituted imidazolidin-2-one derivative of the formula:

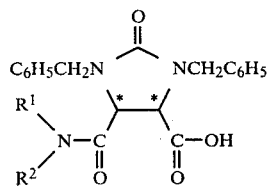

wherein $R^1$ is a $C_1$–$C_4$ alkyl group or benzyl and $R^2$ is a group of the formula:

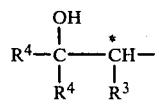

wherein the carbon atom accompanied with an asterisk (*) is an asymmetric carbon atom, $R^3$ is a $C_1$–$C_4$ alkyl group, phenyl or benzyl and $R^4$ is a benzyl or phenyl group optionally substituted with at least one $C_1$–$C_4$ alkyl or $C_1$–$C_4$ alkoxy group.

2. The optically active imidazolidin-2-one derivative according to claim 1, wherein $R^1$ is methyl, ethyl or benzyl, $R^3$ is methyl, isobutyl, benzyl or phenyl and $R^4$ is benzyl, phenyl, 2-methoxyphenyl, 2-isopropoxyphenyl or 2-isopropoxy-5-methylphenyl.

3. 1,3-Dibenzyl-cis-4-carboxy-5-[N-methyl-N-(R)- or (S)-(1-methyl-2,2-diphenyl-2-hydroxyethyl)carbamoyl]imidazolidin-2-one.

4. 1,3-Dibenzyl-cis-4-carboxy-5-[N-benzyl-N-(R)- or (S)-(1-methyl-2,2-diphenyl-2-hydroxyethyl)carbamoyl]imidazolidin-2-one.

5. 1,3-Dibenzyl-cis-4-carboxy-5-[N-methyl-N-(R)- or (S)-(1-isobutyl-2,2-dibenzyl-2-hydroxyethyl)carbamoyl]imidazolidin-2-one.

6. 1,3-Dibenzyl-cis-4-carboxy-5-[N-methyl-N-(R)- or (S)-{1-benzyl-2,2-di(2-isopropoxyphenyl)-2-hydroxyethyl}carbamoyl]imidazolidin-2-one.

7. 1,3-Dibenzyl-cis-4-carboxy-5-[N-methyl-N-(R)- or (S)-{1-methyl-2,2-di(2-methoxyphenyl)-2-hydroxyethyl}carbamoyl}imidazolidin-2-one.

* * * * *